United States Patent [19]

Steglich et al.

[11] 4,122,090

[45] Oct. 24, 1978

[54] CYCLIC ESTERS OF 3,4-DIHYDROXY-THIOPHENE-1,1-DIOXIDE COMPOUNDS AND 3,4-DIHYDROXY-CYCLOPENTADIENONE COMPOUNDS

[75] Inventors: Wolfgang Steglich, Bonn; Oswald Hollitzer; Alfred Seewald, both of Berlin, all of Fed. Rep. of Germany

[73] Assignee: BASF Aktiengesellschaft, Ludwigshafen am Rhein, Fed. Rep. of Germany

[21] Appl. No.: 801,560

[22] Filed: May 31, 1977

[30] Foreign Application Priority Data

June 5, 1976 [DE] Fed. Rep. of Germany .. 2,625,539

[51] Int. Cl.$^2$ ................... C07D 333/48; C07C 103/52
[52] U.S. Cl. .................. 260/332.1; 260/112.5 R; 260/465 R; 260/553 A; 260/561 R; 560/129; 560/155
[58] Field of Search .................................. 260/332.1

[56] References Cited

U.S. PATENT DOCUMENTS

| 3,306,912 | 2/1967 | Fritz et al. ................ 260/332.1 |
| 3,706,769 | 12/1972 | Rosen et al. ............... 260/332.1 |

Primary Examiner—A. Siegel
Attorney, Agent, or Firm—Keil, Thompson & Shurtleff

[57] ABSTRACT

Cyclic esters of 3,4-dihydroxy-thiophene-1,1-dioxide and of the corresponding cyclopentadienone compound, and their manufacture. The compounds can be used as "solid forms" of phosgene, thiophosgene or oxalyl chloride, or as acyl transfer agents.

4 Claims, No Drawings

CYCLIC ESTERS OF 3,4-DIHYDROXY-THIOPHENE-1,1-DIOXIDE COMPOUNDS AND 3,4-DIHYDROXY-CYCLOPENTADIENONE COMPOUNDS

The present invention relates to cyclic esters of 3,4-dihydroxy-thiophene-1,1-dioxide and of the corresponding cyclopentadienone compound, of the general formula (1)

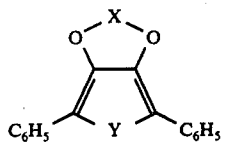
(1)

where X is $> C=O$, $> C=S$ or

and Y is $> SO_2$ or $> C=O$.

Accordingly, the compounds according to the invention are 3,4-carbonyldioxy-2,5-diphenyl-thiophene-1,1-dioxide, 3,4-thiocarbonyldioxy-2,5-diphenyl-thiophene-1,1-dioxide and 3,4-(dicarbonyldioxy)-2,5-diphenyl-thiophene-1,1-dioxide, 3,4-carbonyldioxy-2,5-diphenyl-cyclopentadienone, 3,4-thiocarbonyl-2,5-diphenyl-cyclopentadienone and 3,4-(dicarbonyldioxy)-2,5-diphenyl-cyclopentadienone.

The above compounds may be obtained by reacting a compound of the formula (2)

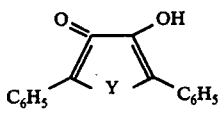

where Y has the above meanings, with a reactive derivative of carbonic acid, thiocarbonic acid or oxalic acid, advantageously in a solvent and in the presence or absence of an acid-binding agent.

3,4-Dihydroxy-2,5-diphenyl-thiophene-1,1-dioxide is a known compound and can be obtained in accordance with processes described in the literature, for example by C. G. Overberger et al, J. Amer. Chem. Soc. 72, (1950), 2856 or M. Chaykovsky et al, J. Org. Chem. 37. (1972), 2018, whilst 3,4-dihydroxy-2,5-diphenyl-cyclopentadienone can be obtained, for example, by the method described by L. Claisen and Th. Evan, Liebigs Ann. Chem. 284, (1895), 264.

Preferred reactive derivatives of carbonic acid, thiocarbonic acid or oxalic acid are the acid chlorides, such as phosgene, thiophosgene or oxalyl chloride. However, compounds such as, for example, carbonyl-diimidazole can also be used.

Advantageous solvents to use are aprotic solvents which are inert under the reaction conditions, dialkyl ethers, eg. diethyl ether, saturated cyclic aliphatic ethers, for example tetrahydrofuran and dioxane, aromatic hydrocarbons, eg. toluene and benzene, chlorinated aliphatic hydrocarbons, eg. methylene chloride or chloroform, and mixtures of the said solvents.

The reaction with an acid chloride can be carried out in the conventional manner in the presence of an acid-binding agent. In particular, aliphatic or cyclic tertiary amines, eg. pyridine or triethylamine, may be used for this purpose.

However, it is particularly advantageous to carry out the reaction without added amine, since it is then unnecessary to remove the amine hydrochloride formed. Under these conditions, the oxalyl chloride reacts sufficiently rapidly even at room temperature, whilst phosgene and thiophosgene may require somewhat longer reaction times or elevated temperatures and/or superatmospheric pressure.

In the presence of an acid-binding amine, the reaction is generally carried out by dissolving the starting compound of the formula (2) in, for example, anhydrous tetrahydrofuran and adding a tertiary amine, eg. pyridine, in an amount equivalent to the acid chloride used, or in excess. The acid chloride is then added slowly, advantageously as a solution in a solvent.

If no amine is added, the procedure followed is, for example in the case of the reaction with oxalyl chloride, to boil the appropriate starting compound with the oxalyl chloride in anhydrous tetrahydrofuran under reflux. With phosgene, quantitative conversion is advantageously achieved at elevated temperatures in an autoclave.

It is advisable to use the acid chloride in excess, with a ratio of from 1:1.2 to 1:2.5. In general, the reactions are carried out with solutions of from 5 to 40% strength by weight.

The reactions are carried out at room temperature or elevated temperatures up to the boiling point of the solvent used. Advantageous temperatures are from 30° to 150° C. In a particularly advantageous embodiment, the reaction is carried out in a closed vessel; in this case, temperatures of from 60° to 100° C. are preferred.

Where necessary, the amine hydrochloride which has precipitated is filtered off after completion of the reaction, and the reaction solution is concentrated by distilling off the solvent, if necessary under reduced pressure, to cause the product to crystallize. This distillation also removes unconverted acid chloride. If desired, the acid chloride, especially phosgene, can also be removed before the distillation, by passing a stream of a dry inert gas, eg. nitrogen, into the mixture. As a rule, the solution which has been concentrated is again filtered and, if necessary, the filtrate is concentrated further until the desired cyclic ester begins to crystallize. The compounds according to the invention can in general be obtained in a crystalline form, in yields of more than 70%, by then leaving the product to stand at from 0° to 25° C.

However, it is also possible to distil off the solvent virtually completely after the reaction has ended, and to treat the residue with water to remove the amine hydrochloride, in which case the desired cyclic ester is obtained pure as the residue after a treatment with, for example, acetone/ether.

This procedure is particularly suitable for the thiocarbonyl compounds which are less prone to hydrolyze.

If no acid-binding organic amine has been added, it can be particularly advantageous to remove the solvent and excess acid chloride by distillation after completion of the reaction. The compounds according to the invention are obtained in a high purity and can be used, without additional purification measures (such as recrystallization or extractive boiling with a suitable solvent), as intermediates for further reactions.

The compounds according to the invention are doubly activated esters and are of importance as highly reactive intermediates which can undergo a diversity of reactions.

Since they undergo substantially the same reactions as phosgene, thiophosgene and oxalyl chloride, they can be used in place of phosgene, thiophosgene and oxalyl chloride as crystalline compounds which are exceptionally suitable for measuring out accurately and exceptionally easy to handle. Accordingly, the compounds of the invention can be used as "solid" phosgene, thiophosgene or oxalyl chloride and have the further particular advantage that they are non-toxic. Reactions of phosgene which the compounds according to the invention also undergo may be found, for example, in the review article in Chem. Reviews, 73 (1973), 75 et seq.

The reactions of 3,4-carbonyl-dioxy-2,5-diphenylthiophene-1,1-dioxide with one equivalent of a nucleophilic agent, eg. an amine, alcohol, phenol or carboxylic acid, produce activated intermediates which when reacted, with or without isolation, with a further equivalent of the above compounds, give ureas, urethanes, esters or amides. At the same time the starting compound, namely 3,4-dihydroxy-2,5-diphenylthiophene-1,1-dioxide or -cyclopentadienone, is formed, which can easily be removed from the reaction mixtures by converting it to a salt with aqueous sodium bicarbonate solution or some other alkali metal base or alkaline earth metal base, and can be recovered by acidification and reconverted to an activated derivative.

The reaction with amines, alcohols and phenols can be represented by the following equation:

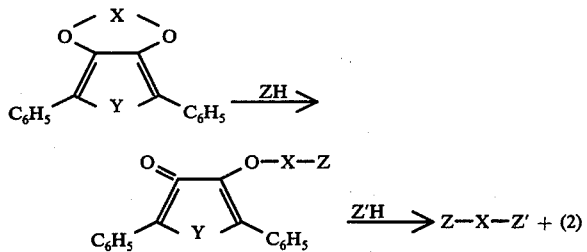

In the equation, X and Y have the above meanings and Z or ZH and Z' or Z'H are nucleophilic structures.

For example, the reaction of 3,4-carbonyldioxy-2,5-diphenylthiophene-1,1-dioxide with 2 moles of aniline in tetrahydrofuran gives a 96% yield of diphenylurea.

This reaction can be modified by carrying it out with one mole of aniline and reacting the intermediate first formed (without having to isolate it), with one mole of another primary or secondary amine, eg. diethylamine, so that unsymmetrically substituted urea compounds, eg. N,N-diethyl-N'-phenyl-urea, are obtained.

Similar reactions with alcohols, eg. benzyl alcohol, in tetrahydrofuran at room temperature, followed by reaction with an amine or an aminoacid ester, eg. L-valine tert.-butyl ester, give the corresponding urethane compounds. As is shown in the example, virtually quantitative yields are obtained.

The reaction of 3,4-(dicarbonyldioxy)-2,5-diphenyl-thiophene-1,1-dioxide with 2 moles of benzylamine gives a 90% yield of oxalic acid dibenzylamide. The stepwise reaction, similar to the manufacture of unsymmetrically substituted ureas, gives mixed oxalyldiamides, which can virtually not be prepared by other methods.

The reaction of 3,4-carbonyldioxy-2,5-diphenylthiophene-1,1-dioxide with pyrocatechol in tetrahydrofuran gives pyrocatechol carbonate, which is a known compound, in a simple manner and in high yields, even at room temperature.

Reactions with carboxylic acids are of particular importance; in these, the intermediate obtained can be used as a reactive compound for transferring acyl radicals. Accordingly, the compounds of the formula (1) provide a new activating agent for peptide syntheses.

An acyl transfer reaction can be represented by the following equation:

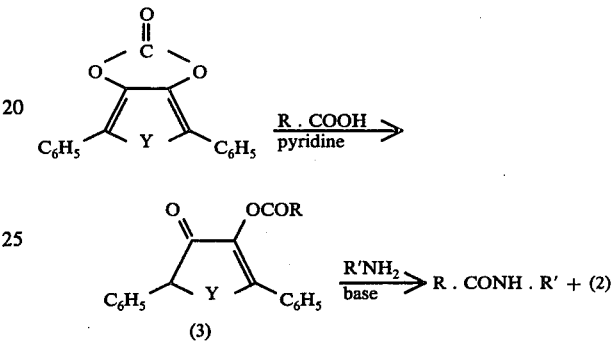

3,4-Carbonyldioxy-2,5-diphenyl-thiophene-1,1-dioxide is reacted with a carboxylic acid to give the mixed anhydride of a vinylogous sulfonic acid of the formula (3), hereinafter also referred to as the activated ester. The activated esters of the formula (3) are readily crystallized, stable compounds which, for example, rapidly react with a primary or secondary amine, advantageously in the presence of tertiary amines, eg. pyridine or triethylamine, to give the corresponding amide. It is particularly advantageous that on addition of the amine the activated esters form orange-red anions, the disappearance of which, accompanied by a change of color to pale yellow, indicates the end of the reaction. The sulfone starting material of the formula (2), formed alongside the amide, can easily be removed by extraction by shaking with aqueous bicarbonate. However, the acyl transfer reactions can also be carried out as one-vessel reactions, without isolating the activated esters.

The reaction of a compound according to the invention, of the formula (1), with a carboxylic acid is advantageously carried out in an anhydrous aprotic solvent in the presence of a tertiary organic amine. The resulting mixed anhydride of the formula (3) reacts extremely well as an acyl transfer agent under mild reaction conditions, giving excellent yields; for example it can be used for reaction with aminoacid esters, for the manufacture of peptides. Simple esters of 3,4-dihydroxy-2,5-diphenylthiophene-1,1-dioxide, corresponding to the formula (3), for example 2,5-diphenyl-3-keto-4-propionyloxy-2,3-dihydrothiophene-1,1-dioxide, can also be manufactured by a conventional acylating method.

However, the surprising advantage, to be singled out particularly, of the reaction of a compound of the invention, of the formula (1), with a carboxylic acid resides in the fact that dicyclohexylcarbodiimide (DCC) is not required for the manufacture of the activated ester of the formula (3). The compounds of the formula (3) are obtained in a readily crystallized and therefore very pure form and are relatively stable on storage. The high reactivity permits the synthesis of sterically hindered peptides which can only be obtained with great difficulty, if at all, by other methods. For example, the dipeptides described in German Published Application DAS 1,936,159, which are used as sweeteners, and the carboxylic acid amides described in German Published Application DAS 2,307,263 can readily be manufactured with the aid of the compounds according to the invention. Furthermore, the use of the compounds according to the invention as intermediates opens up a new method of synthesis of antamanide, a cyclic decapeptide obtained from the L-aminoacids alanine, phenylalanine, proline and valine. Antamanide is a constituent of the death cup Amanita phalloides.

By reacting an activated ester of the formula (3) with an o-nitrophenol it is possible to prepare, for example, the o-nitrophenyl esters which are frequently difficult to obtain by using DCC; this reaction is shown by the following equation:

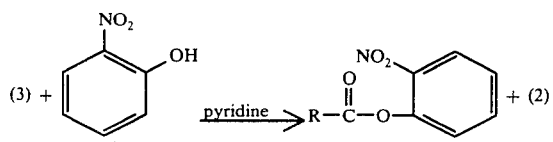

As disclosed in the literature, eg. J. Org. Chemistry 38, (1973), 3565 et seq., or J. Amer. Chem. Soc. 96, (1974), 2234, the o-nitrophenyl esters may be used for further reactions.

The activated esters of type (3) react with alcohols, and also with phenols, thiophenols or mercaptans, to form esters. For example, activated propionic acid and benzyl alcohol in tetrahydrofuran, in the presence of triethylamine, give a very good yield of benzyl propionate.

The formation of cyclic carbonates from 3,4-carbonyldioxy-2,5-diphenyl-thiophene-1,1-dioxide and an o-diphenol, for example pyrocatechol, to give the carbonyldioxy compound of pyrocatechol, should also be mentioned.

A further possible use of the compounds is as dehydrating agents. For example, the oximes of aromatic aldehydes are smoothly converted to the corresponding nitriles.

The Examples further show that the corresponding isocyanates can be obtained from the reaction product of a cyclic carbonate of the formula I with a primary amine.

The novel cyclic esters can also be prepared on polymeric carriers. Since they undergo the same reactions as phosgene, thiophosgene and oxalyl chloride and since the polymeric material can easily be reactivated, the advantages over, for example, carbodiimides on the same polymer are self-evident.

As far as peptide chemistry is concerned, the invention provides novel polymeric activated esters which are distinguished by a high reactivity and by their ability to form a salt with the amine component.

In this context it is particularly advantageous that the manufacture of the polymeric activated esters does not require any dicyclohexylcarbodiimide, so that it is unnecessary to elute the urea which is formed when dicyclohexylcarbodiimide is employed. The % proportion of activated ester lies within the ranges which have been disclosed for other polymeric activated esters.

To manufacture the polymeric cyclic esters it is possible to start, for example, from commercial Merrifield resin, which is reacted with benzylmercaptan in the presence of a base. The further steps are then carried out under similar conditions to those which apply in the case of the monomeric compounds.

A. EXAMPLES OF COMPOUNDS ACCORDING TO THE INVENTION

EXAMPLE 1

3,4-Carbonyldioxy-2,5-diphenyl-thiophene-1,1-dioxide

Without the addition of an amine 10 g of 4-hydroxy-3-oxo-2,5-diphenyl-2,3-dihydrothiophene-1,1-dioxide and 50 ml of a 20% strength by weight solution of phosgene in tetrahydrofuran are heated at 80° C. in an autoclave for 24 hours. The solvent and excess phosgene are then distilled off and pure 3,4-carbonyldioxy-2,5-thiophene-1,1-dioxide is obtained as the residue.

EXAMPLE 2

With the addition of an amine 100 ml of a 20% strength by weight solution of phosgene in toluene (0.2 mole) are added dropwise at 20° C. to 30 g of 4-hydroxy-3-oxo-2,5-diphenyl-2,3-dihydrothiophene-1,1-dioxide and 17 ml of pyridine in 600 ml of dry tetrahydrofuran, whilst stirring vigorously. After one hour the pyridine hydrochloride which has precipitated is filtered off and the filtrate is freed from excess phosgene, using a stream of dry nitrogen, and concentrated under reduced pressure to two-thirds of the original volume. It is filtered again and the filtrate is concentrated until 3,4-carbonyldioxy-2,5-diphenylthiophene-1,1-dioxide crystallizes. After standing overnight at 0° C., 24 g, that is to say a 73% yield, of yellow-green fluorescent small needles which decompose at 250° C. are obtained.

$C_{17}H_{10}O_5S$ (326.3): Calculated: C 62.57; H 3.09; Found: C 62.51; H 3.15

4-Hydroxy-3-oxo-2,5-diphenyl-2,3-dihydrothiophene-1,1-dioxide is recovered by adding sodium hydroxide solution to the residue obtained after evaporation of the mother liquor, filtering the mixture and acidifying the filtrate.

EXAMPLE 3

3,4-(Dicarbonyldioxy)-2,5-diphenylthiophene-1,1-dioxide 6 g of 3-hydroxy-4-oxo-2,5-diphenyl-2,5-dihydrothiophene-1,1-dioxide, 40 ml of tetrahydrofuran and 5 ml of oxalyl chloride are boiled under reflux for 2 hours. After filtering the reaction mixture and distilling off the tetrahydrofuran, 6.8 g, that is to say 96% of theory, of the activated oxalate are obtained as the residue. This is a yellow powder the color of egg yolk and decomposes at 245° to 250° C.

$C_{18}H_{10}O_6S$ (354.3): Calculated: C 61.01; H 2.85; Found: C 61.00; H 2.86

EXAMPLE 4

3,4-Carbonyldioxy-2,5-diphenyl-cyclopentadienone 40 ml of a 20% strength by weight solution of phosgene in toluene are added to 10 g of 4-hydroxy-2,5-diphenyl-4-cyclopentene-1,3-dione and 6 g of pyridine in 150 ml of dry tetrahydrofuran. After stirring the mixture for two hours, the pyridine hydrochloride which has precipitated is filtered off. The dark red filtrate is concentrated and 10.5 g (96%) of pure 3,4-carbonyldioxy-2,5-diphenyl-cyclopentadienone are obtained in the form of black-violet crystals which slowly decompose at above 100° C.

$C_{18}H_{10}O_4$ (290.3): Calculated: C 74.46; H 3.47; Found: C 74.47; H 3.99

EXAMPLE 5

3,4-Thiocarbonyldioxy-2,5-diphenylthiophene-1,1-dioxide 6.5 ml of pyridine are added dropwise to 12 g of 3-hydroxy-4-oxo-2,5-diphenyl-2,3-dihydrothiophene-1,1-dioxide in 150 ml of dry tetrahydrofuran. 4.55 ml of thiophosgene are then added, whilst cooling with ice and stirring.

After the mixture has been left to stand for 90 minutes, the tetrahydrofuran and unconverted thiophosgene are distilled off, the residue is digested with 300 ml of ice water and the precipitate is filtered off and washed several times with water. The filter cake is dried in air. The yield is 11.5 g of crude product and, after boiling thoroughly with acetone/ether (1:3, volume/volume) this gives 10.1 g, that is to say 75% of theory, of the thiocarbonate in analytical purity. This is a greenish yellow powder which decomposes at above 240° C., becomes solid again and melts again at about 290° C.

$C_{17}H_{10}O_4S_2$ (342.4): Calculated: C 59.64; H 2.94; Found: C 60.04; H 2.85

B. EXAMPLES OF REACTIONS WITH THE COMPOUNDS ACCORDING TO THE INVENTION

Examples of the preparation of ureas

N,N-Diphenylurea 3.26 g of 3,4-carbonyldioxy-2,5-diphenylthiophene-1,1-dioxide in 25 ml of dry tetrahydrofuran are left to stand with 1.86 g of aniline for 30 minutes and during the initial period an exothermic reaction takes place. After the reaction has ended, the mixture is partitioned between ether and aqueous 1N sodium hydroxide solution and the organic phase is washed with water and dried over magnesium sulfate. The yield is 2.02 g, that is to say 96% of theory and the melting point is 244°–247° C. (melting point quoted in the literature 235°–239.5° C.).

N,N-Diethyl-N'-phenylurea 0.93 g of aniline is added to 3.26 g of 2,4-carbonyldioxy-2,5-diphenylthiophene-1,1-dioxide in 25 ml of dry tetrahydrofuran. The mixture is left to stand for 30 minutes at 20° C., 0.73 g of diethylamine is added and the mixture is left to stand for a further 40 minutes. After distilling off the tetrahydrofuran, the residue is taken up in chloroform and the chloroform solution is washed successively with aqueous 1N hydrochloric acid and twice with aqueous sodium carbonate solution and water. After drying over magnesium sulfate and evaporating under reduced pressure, 1.4 g of slightly yellowish crystals which, as the crude product, have a melting point of 81°–85° C. (melting point quoted in the literature of 85° C.) remain.

Examples of further unsymmetrically substituted urea compounds which are prepared in the indicated manner with the aid of 2,4-carbonyldioxy-2,5-diphenylthiophene-1,1-dioxide are: N-(2-benzthiazolyl)-N'-methylurea, N-phenyl-N'-(2-methyl-cyclohexyl)urea, N-(3-trifluoromethyl-phenyl)-N',N'-dimethyl-urea, N-cyclooctyl-N',N'-dimethylurea, N-4-fluorophenyl-N'-carboxymethoxy-N'-methyl-urea and N-(4-chlorophenyl)-N'-methyl-N'-(butyn-1-yl)-urea.

The melting points obtained for these compounds when they are prepared in the above way correspond to the melting points quoted in the literature.

Example of the preparation of a urethane

N-Benzyloxycarbonyl-L-valine tert.-butyl ester (a) Activated carbonic acid benzyl ester 3.26 g of 2,4-carbonyldioxy-2,5-diphenylthiophene-1,1-dioxide and 1.08 g of benzyl alcohol are left to stand in 40 ml of dry tetrahydrofuran for 12 hours at 20° C. During this time the intermediate product of formula (3) precipitates. The tetrahydrofuran is distilled off and the residue is washed with ether. The yield is 3.95 g, that is to say 95% of theory, and the melting point 169° C. The NMR spectrum shows only the expected signals.

(b) N-Benzyloxycarbonyl-L-valine tert.-butyl ester 2.1 g of the compound obtained as described in a) are suspended in 300 ml of tetrahydrofuran and 0.90 g of Val-OBut, 1 ml of pyridine and 0.5 ml of triethylamine are added. The red coloration changes to yellow after about 30 minutes. The mixture is left to stand for a further 30 minutes and worked up by the method described in the example for N,N-diethyl-N'-phenylurea. The yield is 1.51 g, that is to say 99% of theory, of an oil, which on examination by NMR shows only the signals of the expected product.

Example of the preparation of an oxalic acid diamide

Oxalic acid dibenzylamide 3.54 g of 3,4-(dicarbonyldioxy)-2,5-diphenylthiophene-1,1-dioxide and 2.4 g of dibenzylamine in 50 ml of dry tetrahydrofuran are stirred at room temperature for 1 hour. After working up in the conventional manner, 2.55 g (94%) of oxalic acid dibenzylamide are obtained.

Example of the preparation of an ester

Benzyl propionate:

(a) Activated propionic acid ester 10 g of 4-hydroxy-3-oxo-2,5-diphenyl-2,3-dihydrothiophene-1,1-dioxide and 2.62 g of pyridine are dissolved in 100 ml of tetrahydrofuran. 3.06 g of propionyl chloride in 50 ml of tetrahydrofuran are added to this solution. After stirring for two hours at room temperature, the solvent is stripped off, the residue is taken up in chloroform and the chloroform solution is shaken with 1 N HCl and saturated sodium bicarbonate solution, washed with water and dried over $MgSO_4$. After stripping off the solvent and recrystallizing the residue from petroleum ether/ethyl acetate, 11 g (92%) of activated propionic acid are obtained.

$C_{19}H_{16}O_5S$ (356.4): Calculated: C 64.03; H 4.53; S 9.00; Found: C 64.04; H 4.61; S 9.35

(b) Benzyl propionate 3.56 g of the compound obtained as described in (a) are dissolved in 50 ml of chloroform. 1.2 g of benzyl alcohol and 1 ml of triethylamine are added. The red coloration which appears initially changes to pale yellow within 2 hours. After working up as described under a), 1.5 g (91%) of benzyl propionate, which is pure according to NMR, are obtained.

Example of the elimination of water

Conversion of an oxime into its nitrile:

1.55 g of the oxime of p-chlorobenzaldehyde and 3.5 g of 3,4-carbonyldioxy-2,5-diphenylthiophene-1,1-dioxide in 25 ml of dry toluene are heated at 90° for 45 minutes. The mixture is then washed with aqueous sodium bicarbonate solution and water. After drying over magnesium sulfate and stripping off the solvent, 1.25 g (91%) of p-chlorobenzonitrile which has the melting point quoted in the literature are obtained.

Examples of activated esters and of acyl transfer reactions

Activated ester of N-tert.-butoxycarbonyl-L-phenylalanine 1.96 g of 3,4-carbonyldioxy-2,5-diphenylthiophene-1,1-dioxide, 2.33 g of Boc-Phe-OH and 0.49 ml of pyridine are stirred in 50 ml of absolute methylene chloride for 2 hours (evolution of $CO_2$). The reaction mixture is washed three times with 20% strength citric acid solution and three times with saturated sodium bicarbonate solution, again with citric acid solution and with water, and dried over magnesium sulfate. The solvent is distilled off under reduced pressure. The yield is 2.63 g, that is to say 96% of theory; the melting point is 169° C., and 170° C. after recrystallization from ethyl acetate/petroleum ether.

$C_{30}H_{29}NO_7S$ (547.6): Calculated: C 65.80; H 5.33; N 2.56; S 5.85; Found: C 65.80; H 5.41; N 2.63; S 5.77

N-tert.-Butoxycarbonyl-L-phenylalanyl-L-valine methyl ester 0.40 g of valine methyl ester hydrochloride is added to a reddish orange solution of 1.10 g of the compound obtained above and 0.61 g of triethylamine in 50 ml of dry methylene chloride, the color immediately changing to pale yellow. The mixture is stirred for a further 15 minutes at 20° C. and worked up as indicated above. The yield is 0.70 g, that is to say 93% of theory.

Activated ester of Boc-Phe from 3,4-dicarboxyldioxy-2,5-diphenylthiophene-1,1-dioxide 2.65 g of Boc-Phe and 1 ml of pyridine are added to 4.2 g of 3,4-dicarbonyldioxy-2,5-diphenylthiophene-1,1-dioxide in 40 ml of dry tetrahydrofuran. Vigorous evolution of gas takes place. After stirring for 12 hours, the reaction mixture is worked up in the conventional manner. The yield of 4.6 g corresponds to 84% of theory. The product is identical to the compound prepared from 3,4-carbonyldioxy-2,5-diphenylthiophene-1,1-dioxide.

N-Benzyloxycarbonyl-L-prolyl-L-valine tert.-butyl ester, using 3,4-carbonyldioxy-2,5-diphenyl-cyclopentadienone 2.050 g of 3,4-carbonyldioxy-2,4-diphenyl-cyclopentadienone are added to 1.763 g of Z-Pro-OH and 0.560 g of pyridine in 15 ml of absolute tetrahydrofuran. The mixture is left to stand for 50 minutes, 1.220 g of L-valine tert.-butyl ester are added and after 1 hour working up is carried out in the conventional manner. The yield is 2.146 g, that is to say 53% of theory, of N-benzyloxycarbonyl-L-prolyl-L-valine tert.-butyl ester with a melting point of 108°–111° C.

TABLE 1

4-Acyloxy-3-oxo-2,5-diphenyl-2,3-dihydrothiophene-1,1-dioxide according to formula(3) [a]

| R (R-CO in the case of N-acylamino acids) | Yield (%) [b] | Method [c] | Melting point (° C) [d] | $[\alpha]25$ 546 | (c = 1 in methylene chloride) [d] |
|---|---|---|---|---|---|
| $C_2H_5$ | 92 | C | 101–102 | | $C_{19}H_{16}O_5S$ (356.4) |
| | | | | Calculated: | C 64.03, H 4.53, S.9.00 |
| | | | | Found: | C 64.04, H 4.61, S.9.35; |
| $C(CH_3)_3$ | 91 | C | 177–178 | | $C_{21}H_{20}O_5S$ (384.4) |
| | | | | Calculated: | C 65.61, H 5.24 |
| | | | | Found: | C 65.59, H 5.21 |
| Z-Val | 95 | A | 161–163 | 43.5° | |
| | 82 | B | | | |
| Z-Pro | 99 | A | 104–106 | 54.3° | |
| | | | | | $C_{29}H_{25}NO_7S$ (531.6) |
| | | | | Calculated: | C 65.52, H 4.74, N 2.63 |
| | | | | Found: | C 65.46, H 4.79, N 2.70; |
| Boc-Pro | 98 | A | 158–159 | 55.7° | |
| | | | | | $C_{26}H_{27}NO_7S$ (497.5) |
| | | | | Calculated: | C 62.67, H 5.47, N 2.81, S 6.44 |
| | | | | Found: | C 62.63, H 5.29, N 2.87, S 6.56; |
| Boc-Phe | 96 | A | 170 | 39.0° | |
| | | | | | $C_{30}H_{29}NO_7S$ (547.6) |
| | | | | Calculated: | C 65.80, H 5.33, N 2.56, S 5,85 |
| | | | | Found: | C 65.80, H 5.41, N 2.63, S 5.77 |
| Boc-Met | 91 | A | 193–194 | 37.4° | |
| | | | | | $C_{26}H_{29}NO_7S_2$ (531.7) |
| | | | | Calculated: | C 58.74, H 5.50, N 2.63 |
| | | | | Found: | C 58.76, H 5.40, N 2.66 |

[a] All the compounds gave correct elementary analyses
[b] Crude yields of the products which, according to spectroscopy, are the pure compounds
[c] A: from the carboxylic acid, pyridine and (2); B: from the carboxylic acid, (1) and dicyclohexylcarbodiimide; C: from the carboxylic acid chloride, (1) and pyridine
[d] Values for the recrystallized compounds, which are analytically pure. (3c)–(3g) are in the form of mixtures of diastereomers.

The Table shows that the yields obtained when (1a) is used as the starting compound (process A) are substantially higher than those obtained with the conventional methods B and C.

TABLE 2

| N-Acyl dipeptide ester [a] | | | Melting point (° C) | | |
|---|---|---|---|---|---|
| Compound | Reaction time (min.) Base added | yield (%) | Melting point quoted in the literature | | Literature |
| Z-Val-Val-OMe | 120, triethylamine | 97 | 104 | 107–109 | [7] |
| Z-Pro-Val-OtBu | 10, pyridine | 94 | 111–112 | 114–115 | [8] $C_{22}H_{32}N_2O_5$ (404.5) |
|  | 120, triethylamine | 97 | 112–114 | [c] |  |
|  | 60, pyridine [b] | 94 | 107–111 |  | Calculated: |
|  |  |  |  |  | C 65.32 H 7.97 |
|  |  |  |  |  | N 6.93 |
|  |  |  |  |  | Found: |
|  |  |  |  |  | C 65.30 H 8.02 |
|  |  |  |  |  | N 6.72 |
| Boc-Phe-Val-OMe | 15, triethylamine | 93 | 110–112 | 120–122 | [9] |
| Boc-Met-Ala-OMe | 120, triethylamine | 99 | 72 | 84–85 | [10] |

[a] Yield and melting point of the crude products after drying under reduced pressure produced by an oil pump.
[b] Without isolation of (3d) after 60 minutes pre-activation of Z-Pro-OH with (2) and pyridine
[c] $[\alpha]_D^{25} = -34.0°$; literature [8]: $-34.3°$ (in each case c = 1 in DMF)
[d] $[\alpha]_D^{25} = -11.1°$; literature [9]: $-11°$ (c = 1 or 0.5 in DMF)

As Table 2 shows, even sterically more difficult dipeptide derivatives are formed within a few minutes in virtually quantitative yields. The products are characterized without recrystallization and in most cases are analytically pure. Examination of the corresponding N-trifluoroacetyldipeptide methyl ester by gas chromatography shows that the activation and the peptide coupling to Z-Pro-Val-OMe proceed without racemization.

Competitive-reaction experiments show that the activated esters according to formula (3) are more effective acyl transfer agents than the p- and o-nitrophenyl esters frequently used in peptide syntheses (M. Bodanszky et al., J.Org.Chem. 38 (1973) 3365). Thus, a mixture of equimolar amounts of 4-pivaloyloxy-3-oxo-2,5-diphenyl-2,3-dihydrothiophene-1,1-dioxide, p-nitrophenyl acetate and benzylamine gives 97% of N-benzylpivalamide and 3% of N-benzylacetamide (NMR and GC analysis) after 2 hours at room temperature, although pivaloyloxy-3-oxo-2,5-diphenyl-2,3-dihydrothiophene-1,1-dioxide sterically has considerable disadvantages.

With valine methyl ester, 4-propionyloxy-3-oxo-2,5-diphenyl-2,3-dihydrothiophene-1,1-dioxide and o-nitrophenyl acetate form a mixture of 99% of the N-propionyl derivative and only 1% of the N-acetyl derivative. The high reactivity of the esters 3 towards amines is probably due to the fact that the enolate group in the anion accelerates the aminolysis by intramolecular general base catalysis.

Particularly advantageously, the intermediate products according to the invention can be used for the peptide synthesis in the form of a polymer reagent, bonded to a resin. Polymeric activated esters can be prepared from commercial Merrifield resin (chloromethylated copolymer of styrene and 2% of 1,4-divinylbenzene).

The polymer reagent obtainable in this way is in many cases equivalent to phosgene, thiophosgene and oxalyl chloride and this opens up new preparative possibilities. The synthesis of the resin and its use for the synthesis of two sterically hindered dipeptides is described below:

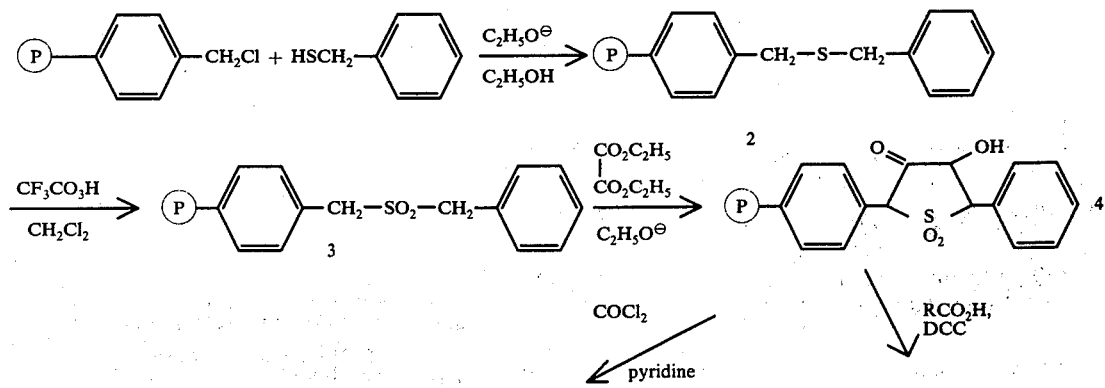

-continued

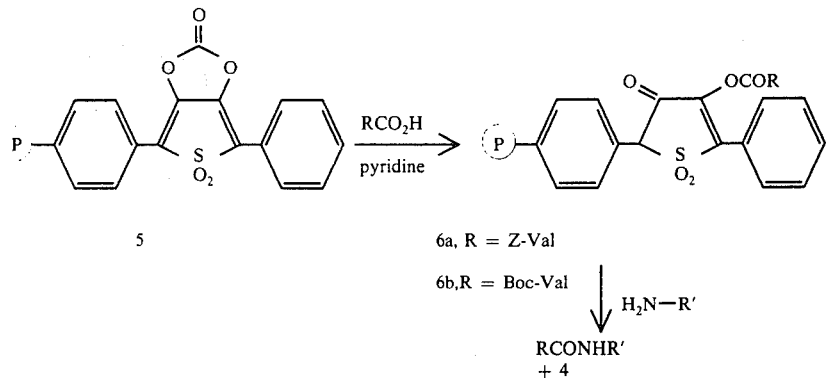

5

6a, R = Z-Val
6b, R = Boc-Val $\downarrow$ H$_2$N—R'

RCONHR'
+ 4

In order to prepare the polymeric thiobenzyl ether 2, Merrifield resin is heated for a prolonged period with sodium mercaptide in ethanol. According to the sulfur analysis, 1.4 mmoles of benzylmercaptan/g of resin are incorporated. The oxidation to the sulfone 3 is carried out with H$_2$O$_2$/trifluoroacetic acid anhydride. The oxidation can be discerned from intense sulfone bands at 1,320 and 1,120 cm$^{-1}$. The condensation reaction with diethyl oxalate to give the ketosulfone 4 proceeds relatively slowly. The IR bands at 1,715 and 1,495 cm$^{-1}$ which are characteristic of 4 are obtained in their full intensity only after boiling twice with sodium ethylate in ethanol (each time for 6 days). If the resin 4 is reacted with phosgene/pyridine in chloroform, the cyclic carbonate 5, which can be recognized from the typical IR band at 1,888 cm$^{-1}$, is formed.

When 5 is stirred with Z-Val-OH and pyridine in methylene chloride (24 hours, 20° C.), the carbonyl band at 1,888 cm$^{-1}$ disappears and the polymeric activated ester 6a forms. A resin which has an identical IR spectrum can also be obtained by reacting 4 with Z-Val-OH and dicyclohexylcarbodiimide (DCC) in DMF. The dicyclohexylurea is removed by eluting with methanol. In order to determine the content of activated aminoacid ester, the resin 6a was reacted with benzylamine. From the amount of Z-L-Val-benzylamide formed, the proportion of active groups introduced is 0.15 mmole of Z-Val/g of resin. If the resin is reacted with Val-OMe in methylene chloride for 130 minutes at 20° C., the Z-dipeptide ester is again formed in a yield of 0.15 mmole/g of resin.

In a second synthesis of the polymeric ketosulfone, the proportion of active groups introduced can be improved. With Boc-Val-OH and DCC in DMF, resin 4 gives a polymeric activated ester 6b, which with benzylamine gives 0.48 mmole of Boc-L-valine-benzylamide/g of resin. If the resin (2.3 molar excess) is stirred with Val-OMe in methylene chloride for 200 minutes at 20° C., Boc-Val-OMe, which according to the melting point, OR and NMR is identical to the authentic compound, can be isolated in 41% yield.

Preparation of the polymeric activated carbonate 5

(1) Polymeric benzyl sulfide 2

25 g of Merrifield resin (Merck-Schuchardt) and 12 ml of benzylmercaptan are added to a solution of 2.3 g of sodium in 200 ml of ethanol and the mixture is stirred carefully with a KPG stirrer. After 20–40 hours at 70° C., the resin is filtered off and washed successively with methanol, water, glacial acetic acid, water and methanol. It is dried at 80°–100° C. under reduced pressure produced by an oil pump. Sulfur content: 4.36%; chlorine content: 0.29%.

(2) Polymeric benzylsulfone 3

40 ml of 30% strength H$_2$O$_2$ are added carefully to 40 ml of trifluoroacetic acid anhydride in 100 ml of methylene chloride, whilst cooling with ice. After adding 15 g of resin 2, the mixture is stirred for 10–15 hours at 20° C. and the resin is then filtered off, washed successively with methylene chloride, water and methanol and dried at 80°–100° C. under reduced pressure produced by an oil pump.

IR (KBr): intense bands at 1,320 and 1,120 cm$^{-1}$ (—SO$_2$—).

Sulfur content: 3.90%.

(3) Polymeric ketosulfone 4

40 ml of diethyl oxalate and 10 g of resin 3 are added to a solution of 2 g of sodium in 400 ml of ethanol. The mixture is heated under reflux for 3 days and during this time the solution develops a brown coloration. The resin is then filtered off, washed successively with ethanol (5 × 100 ml), water (10 × 100 ml), glacial acetic acid (5 × 100 ml), water (5 × 100 ml) and methanol (5 × 100 ml) and dried for several hours at 80°–100° C. under reduced pressure produced by an oil pump. In order to achieve complete conversion, the resin thus obtained is subjected to a further condensation reaction with diethyl oxalate.

IR (KBr): characteristic bands at 1,715 and 1,495 cm$^{-1}$, the intensity of which increases after the second condensation reaction.

Sulfur content: 3.68%.

(4) Polymeric activated carbonate 5

2–5 ml of phosgene are added to 8 g of the polymeric ketosulfone 4 in 100 ml of chloroform and 5 ml of pyridine. The mixture is stirred for about 5 hours and the resin is filtered off and, in order to remove the pyridine hydrochloride, is extracted in a Soxhlet apparatus with phosgene-containing chloroform (acetone/solid carbon dioxide condenser). The resin is dried at 60° C. under reduced pressure produced by an oil pump.

IR (KBr): 1,888 cm$^{-1}$ (—O—CO—O—).

Use of the polymers 4 and 5 for amide and peptide syntheses (5) Polymeric activated ester of Z-L-valine 6a (a) From resin 5: 5 g of polymeric activated carbonate 5 are stirred with 1.25 g of Z-Val-OH and 1 ml of pyridine in 50 ml of absolute tetrahydrofuran for 12 hours at 20° C. The resin is filtered off, washed with THF and dried at 60° C. under reduced pressure produced by an oil pump. Unconverted Z-Val-OH can be recovered after evaporating the reaction and wash solutions.

(b) From resin 4: 5 g of the polymeric ketosulfone 4 are stirred with 2.51 g of Z-Val-OH and 2.06 g of dicyclohexylcarbodiimide in 30 ml of DMF for 2 hours at 0° C. and for 3 hours at 20° C. The resin is filtered off, washed thoroughly with methanol and dried at 60° C. under reduced pressure produced by an oil pump. The resins 6a obtained by the two routes had the same IR spectrum.

(6) Synthesis of Z-L-valine benzylamide 3 g of the activated ester 6a obtained as described in a) are stirred with 0.5 g of benzylamine in 40 ml of chloroform for 2 hours at 20° C. The resin is filtered off and washed thoroughly with chloroform and after extracting the filtrates by shaking with N HCl, sodium carbonate solution and water and drying and evaporating, 0.150 g of Z-Val benzylamide, which is identical to an authentic comparative preparation, is obtained. From this, the proportion of active groups introduced is calculated as 0.15 mmole of Z-Val-OH/g of resin 6a. The IR spectrum of the resin which has been obtained after the reaction agrees with 4.

(7) Z-Val-OMe 5.61 g of the resin 6a obtained according to Instruction (5b) are stirred in 40 ml of chloroform with 0.50 ml of pyridine and 0.350g of L-valine methyl ester hydrochloride for 130 minutes. The resin is filtered off and washed with 200 ml of chloroform and the filtrate is worked up as described in the previous Example. The yield is 0.300 g of Z-Val-Val-OMe and the melting point of the crude product is 120° C.; according to the IR and NMR spectrum, this product is identical to the authentic comparative preparation.

(8) Polymeric activated ester of Boc-L-valine 6b 10 g of resin 4 +), 6.5 g of Boc-Val-OH and 6.2 g of DCC were stirred in 30 ml of dimethylformamide for 2 hours at 0° C. and then for a further 3 hours at 20° C. The resin is filtered off, washed thoroughly with methanol and dried at 60° under reduced pressure produced by an oil pump.

+) different batch of resin from that used for the preparation 6a (9) Boc-L-valine benzylamide 2.22 g of the polymeric activated ester 6b in 30 ml of chloroform are stirred with 1 g of benzylamine for 15 minutes. The resin is filtered off and washed with chloroform and the combined filtrates are extracted by shaking successively with 0.5 N HCl, sodium carbonate solution and water. After drying and evaporating, the product, which is identical to an authentic sample, is obtained in a yield of 0.323 g. This gives a content of 0.48 mmole of Boc-Val-OH/g of resin 6b.

(10) Boc-Val-Val-OMe 7.5 g of the polymeric activated ester 6b (3.5 mmoles of Boc-Val-OH) and 0.250 g of L-valine methyl ester hydrochloride (1.5 mmoles) are stirred in 100 ml of absolute methylene chloride. After adding 3 ml of triethylamine and 1 ml of pyridine, the mixture is stirred for a further 200 minutes. The filtrates are washed successively with 0.5 N HCl, sodium carbonate and water, dried and evaporated under reduced pressure. After recrystallization from ether/petroleum ether, 0.200 g of Boc-Val-Val-OMe is obtained (yield 41%, based on the L-valine methyl ester hydrochloride employed). Melting point 159°–161°; melting point quoted in the literature 165°–166° C.

C. Examples of the preparation of active esters of the formula (3), of reactions of 3,4-carbonyldioxy-2,5-diphenylthiophene-1,1-dioxide and of the further processing of the resulting compounds

1. 3-(Phenylcarbamyloxy)-4-hydroxy-2,5-diphenylthiophene-1,1-dioxide 0.93 g of aniline is added to 3.59 g of 3,4-carbonyldioxy-2,5-diphenylthiophene-1,1-dioxide in 30 ml of hot ethyl acetate and the reaction solution develops a reddish orange coloration for a short time. After boiling under reflux for 20 minutes, the solution is concentrated to half the original volume and filtered. The filter residue is washed in portions with 100 ml of concentrated aqueous $NaHCO_3$ solution and then with 100 ml of 20% strength aqueous citric acid solution.

Yield: 3.7 g (88%), melting point 227° C. (decomposition) after recrystallization from chloroform/petroleum ether $C_{23}H_{17}NO_5S$, calculated: C 65.87; H 4.06; found: C 66.01; H 4.02

2. 3-(Benzylcarbamyloxy)-4-hydroxy-2,5-diphenylthiophene-1,1-dioxide 1.07 g of benzylamine are added to 3.59 g of 3,4-carbonyldioxy-2,5-diphenylthiophene-1,1-dioxide in 30 ml of hot ethyl acetate. The solution is boiled under reflux for 20 minutes and then washed with three times 30 ml of concentrated aqueous $NaHCO_3$ solution and with three times 30 ml of 20% strength aqueous citric acid solution. The wash liquors are extracted with ethyl acetate and the combined organic extracts are dried over magnesium sulfate and evaporated.

Yield: 3.6 g (83%), melting point 200° C. (decomposition) after recrystallization from chloroform/petroleum ether $C_{24}H_{19}NO_5S$: calculated: C 66.51; H 4.39; found: C 66.42; H 4.35

3. 3-(N,N-Diethylcarbamyloxy)-4-hydroxy-2,5-diphenylthiophene-1,1-dioxide 730 mg of diethylamine are added to 3.59 g of 3,4-carbonyldioxy-2,5-diphenylthiophene-1,1-dioxide in 30 ml of hot ethyl acetate. The solution is boiled under reflux for 20 minutes, concentrated to half its volume and filtered. The precipitate is washed in portions with 100 ml of concentrated aqueous $NaHCO_3$ solution and then with 100 ml of 20% strength aqueous citric acid solution.

Yield: 3.4 g (85), melting point 147° C. after recrystallization from chloroform/petroleum ether $C_{21}H_{21}NO_5S$: calculated: S 8.02; found: S 8.15

4. 3-(N,N-Dicyclohexylcarbamyloxy)-4-hydroxy-2,5-diphenylthiophene-1,1-dioxide 1.81 g of dicyclohexylamine are added to 3.59 g of 3,4-carbonyldioxy-2,5-diphenylthiophene-1,1-dioxide in 30 ml of hot ethyl acetate and the solution develops a deep red coloration for a short time. After boiling under reflux for 20 minutes, the solution is concentrated to half its volume and filtered. The precipitate is treated as described in Example C 3.

Yield: 4.36 g (86%), melting point 165° C. after recrystallization from chloroform/petroleum ether $C_{20}H_{33}NO_5S$: calculated: S 6.31; found: S 6.47

5. 3-(Piperidylcarbamyloxy)-4-hydroxy-2,5-diphenylthiophene-1,1-dioxide 850 mg of piperidine are added to 3.59 g of 3,4-carbonyldioxy-2,5-diphenylthiophene-1,1-dioxide in 30 ml of hot ethyl acetate. After boiling under reflux for 20 minutes, the solution is washed three times with 30 ml of concentrated aqueous $NaHCO_3$ solution and three times with 20% strength aqueous citric acid solution. The wash liquids are extracted with ethyl acetate and the combined organic phases are dried over magnesium sulfate. After distilling off the solvent, a yellowish colored product is obtained as the residue and this is recrystallized from chloroform/petroleum ether.

Yield: 3.3 g (80%), melting point 135° C.

$C_{22}H_{21}NO_5S$: calculated: S 7.78; found: S 7.77

6. 3-(4-Morpholinylcarbamyloxy)-4-hydroxy-2,5-diphenylthiophene-1,1-dioxide 870 mg of morpholine are added to 3.59 g of 3,4-carbonyldioxy-2,5-diphenylthiophene-1,1-dioxide in 30 ml of hot ethyl acetate and the solution is boiled under reflux for 30 minutes. The solution is then worked up as described in Example C 5.

Yield: 2.89 g (70%), melting point 174° C. after recrystallization from chloroform/petroleum ether $C_{21}H_{19}NO_6S$: calculated: C 61.02; H 4.60; N 3.39; found: C 61.21; H 4.65; N 3.47

7. O-Ethyl-O'-(3-hydroxy-2,5-diphenylthiophene-1,1-dioxidecarbonate 460 mg of ethanol are added to 3.59 g of 3,4-carbonyldioxy-2,5-diphenylthiophene-1,1-dioxide in 30 ml of ethyl acetate. The solution is boiled under reflux for 2 hours and then washed three times with 30 ml of concentrated aqueous $NaHCO_3$ solution and three times with 20% strength citric acid solution. The wash liquors are extracted with ethyl acetate and the combined organic phases are dried over magnesium sulfate and then evaporated. The residue is recrystallized from cyclohexane.

Yield: 3.01 g (81%), melting point 129° C.

$C_9H_{16}SO_6$: calculated: C 61.29; H 4.30; found: C 61.31; H 4.19

8. O-Isobutyl-O'-(3-hydroxy-2,5-diphenylthiophene-1,1-dioxide)carbonate 740 mg of isobutyl alcohol are added to 3.59 g of 3,4-carbonyldioxy-2,5-diphenylthiophene-1,1-dioxide in 30 ml of ethyl acetate. The solution is boiled under reflux for 2 hours and then worked up as described in Example C 7.

Yield: 2.78 g (69.5%), melting point 132° C. after recrystallization from cyclohexane $C_{21}H_{20}SO_6$: calculated: C 63.0; H 5.0; found: C 62.85; H 4.96

9. O-Phenyl-O'-(3-hydroxy-2,5-diphenylthiophene-1,1-dioxide)carbonate 3.59 g of 3,4-carbonyldioxy-2,5-diphenylthiophene-1,1-dioxide are suspended in 10 ml of acetone and 940 mg of phenol in 5 ml of acetone are added. The mixture is boiled under reflux for 30 minutes and then filtered. The filter residue is washed with 50 ml of concentrated aqueous $NaHCO_3$ solution and then with 50 ml of 20% strength aqueous citric acid solution.

Yield: 3.4 g (81%), melting point 178° C. after recrystallization from chloroform.

$C_{23}H_{16}O_6S$: calculated: C 65.7; H 3.81; found: C 65.1; H 3.90

10. O-Cholesteryl-O'-(3-hydroxy-2,5-diphenylthiophene-1,1-dioxide)-carbonate 3.87 g of cholesterol are added to 3.59 g of 3,4-carbonyldioxy-2,5-diphenylthiophene-1,1-dioxide in 30 ml of hot ethyl acetate. The solution is boiled under reflux for 2 hours and then worked up as described in Example C 7.

Yield: 4.48 g (63%), melting point 119° C. after recrystallization from chloroform/petroleum ether $C_{44}H_{56}O_6S$: calculated: C 74.16; H 7.86; found: C 73.92; H 8.16

11. 3-[N-L(1-Carbomethoxy-ethyl)-carbamyloxy]-4-hydroxy-2,5-diphenylthiophene-1,1-dioxide 1.03 g of L-alanine methyl ester are added to 3.59 g of 3,4-carbonyldioxy-2,5-diphenylthiophene-1,1-dioxide in 30 ml of ethyl acetate. The solution is boiled under reflux for 30 minutes and then washed three times with 30 ml of concentrated aqueous $NaHCO_3$ solution and three times with 20% strength citric acid solution. The wash liquors are extracted with ethyl acetate and the combined organic phases are dried over magnesium sulfate and evaporated.

Yield: 3.73 g (87%), melting point 227° C. (decomposition) (cyclohexane)

$C_{21}H_{19}NO_7S$: calculated: C 58.74; H 4.43; found: C 58.61; H 4.59

12. 3-[N-L(1-Carbomethoxy-2-methyl-propyl)-carbamyloxy]-4-hydroxy-2,5-diphenylthiophene-1,1-dioxide 1.28 g of L-valine methyl ester are added to 3.59 g of 3,4-carbonyldioxy-2,5-diphenylthiophene-1,1-dioxide in 30 ml of ethyl acetate. The solution is boiled under reflux for 30 minutes and then worked up as described in Example C 11.

Yield: 3.88 g (85%), melting point 230° C. (decomposition) (cyclohexane)

$C_{23}H_{23}NO_7S$: calculated: C 60.39; H 5.03; found: C 60.19; H 5.00

13. O-iso-Propyl-O'-(4-hydroxy-2,5-diphenylthiophene-1,1-dioxide)-carbonate 600 mg of isopropanol are added to 3.59 g of 3,4-carbonyldioxy-2,5-diphenylthiophene-1,1-dioxide in 30 ml of ethyl acetate. The mixture is boiled under reflux for 2 hours and then worked up as described in Example C 11.

Yield: 3.32 g (86%), melting point 131° C. (cyclohexane)

$C_{20}H_{18}O_6S$: calculated: C 62.2; H 4.66; found: C 62.05; H 4.70

14.
3-[N-L-(1-Carbethoxy-3-methyl)-butyl-carbamyloxy]-4-hydroxy-2,5-diphenylthiophene-1,1-dioxide 1.59 g of L-leucine ethyl ester are added to 3.59 g of 3,4-carbonyldioxy-2,5-diphenylthiophene-1,1-dioxide in 30 ml of ethyl acetate. The solution is boiled under reflux for 1 hour and then worked up as described in Example C 11.

Yield: 4.12 g (85%), melting point 253° C. (decomposition) (chloroform)

$C_{25}H_{27}NO_7S$: calculated: C 61.86; H 5.57; found: C 61.65; H 5.60

15.
3-(N,N-Diphenylcarbamyloxy)-4-hydroxy-2,5-diphenylthiophene-1,1-dioxide 1.68 g of diphenylamine are added to 3.59 g of 3,4-carbonyldioxy-2,5-diphenylthiophene-1,1-dioxide in 25 ml of dioxane. The solution is boiled under reflux for 45 minutes and then evaporated to dryness. The residue is taken up in 30 ml of ethyl acetate and worked up as described in Example C 11.

Yield: 3.4 g (71.7%), melting point 216° C. (chloroform/petroleum ether)

$C_{29}H_{21}NO_5S$

16.
O-tert.-Butyl-O'-(3-hydroxy-2,5-diphenylthiophene-1,1-dioxide)-carbonate 740 mg of tert.-butyl alcohol are added to 3.59 g of 3,4-carbonyldioxy-2,5-diphenylthiophene-1,1-dioxide in 30 ml of ethyl acetate. The solution is boiled under reflux for 2 hours and then worked up as described in Example C 11.

Yield: 3.16 g (79%), melting point (acetone/petroleum ether)

$C_{21}H_{20}O_6S$: calculated: C 63.00; H 5.00; found: C 62.86; H 5.19

17.
O-(3-Hydroxy-2,5-diphenylthiophene-1,1-dioxide)-S-benzylthiol-carbonate 1.24 g of benzylmercaptan are added to 3.59 g of 3,4-carbonyldioxy-2,5-diphenylthiophene-1,1-dioxide in 30 ml of ethyl acetate. The solution is boiled under reflux for 2 hours and then worked up as described in Example C 11.

Yield: 3.90 g (86.6%), melting point 173° C. (chloroform)

$C_{24}H_{18}O_5S_2$: calculated: C 64.00; H 4.00; found: C 63.91; H 4.11

18. N-Benzyl-N'-phenylurea 540 mg of benzylamine are added to 2.1 g of 3-(N-phenylcarbamyloxy)-4-hydroxy-2,5-diphenylthiophene-1,1-dioxide in 20 ml of ethyl acetate. The solution is boiled under reflux for 1 hour and then washed three times with 25 ml of concentrated aqueous $NaHCO_3$ solution and three times with 20% strength aqueous citric acid solution. The wash liquors are extracted with ethyl acetate and the combined organic phases are dried over magnesium sulfate. After evaporating the filtrate, the crystalline residue is recrystallized from dilute ethanol.

Yield: 1.02 g (90%), melting point 167° C.

$C_{14}H_{14}N_2O$: calculated: C 74.3; H 6.2; found: C 73.95; H 6.15

19. N-Benzyl-N',N'-diethylurea 365 mg of diethylamine are added to 3.16 g of 2-(N-benzyl-carbamyloxy)-4-hydroxy-2,5-diphenylthiophene-1,1-dioxide in 25 ml of ethyl acetate. The solution is boiled under reflux for 1 hour and then worked up as described in Example C 18.

Yield: 876 mg (85%), melting point 170° C. (ethanol)

$C_{12}H_{18}N_2O$: calculated: C 69.00; H 8.74; found: C 69.85; H 8.63

20. N,N-Diethyl-N'-phenylurea 365 mg of diethylamine are added to 2.1 g of 3-(N-phenylcarbamyloxy)-4-hydroxy-2,5-diphenylthiophene-1,1-dioxide in 20 ml of ethyl acetate. The solution is boiled under reflux for 1 hour and then worked up as described in Example C 18.

Yield: 758 mg (79%), melting point 86° C. (methanol)

$C_{11}H_{16}N_2O$: calculated: C 68.75; H 8.33; found: C 68.60; H 8.21

21. 1-Benzyl-carbamylpiperidine 540 mg of benzylamine are added to 2.06 g of 3-(1-piperidylcarbamyloxy)-4-hydroxy-2,5-diphenylthiophene-1,1-dioxide in 20 ml of ethyl acetate. The solution is boiled under reflux for 1 hour and then worked up as described in Example C 18.

Yield: 1.00 g (92%), melting point 165° C. (methanol)

$C_{13}H_{18}N_2O$: calculated: C 71.56; H 8.26; found: C 70.99; H 8.35

22. 1-Benzyl-carbamylmorpholine 540 mg of benzylamine are added to 2.06 g of 3-(4-morpholinylcarbamyloxy)-4-hydroxy-2,5-diphenylthiophene-1,1-dioxide in 20 ml of ethyl acetate. The solution is boiled under reflux for 1 hour and then worked up as described in Example C 18.

Yield: 980 mg (89%), melting point 176° C. (methanol) $C_{12}H_{16}N_2O_2$: calculated: C 65.45; H 7.27; found: C 64.95; H 7.35

23. N,N'-Di-(L-1-carbomethoxy-ethyl)-urea 2.06 g of L-alanine methyl ester are added to 3.59 g of 3,4-carbonyldioxy-2,5-diphenylthiophene-1,1-dioxide in 30 ml of ethyl acetate. The solution is boiled under reflux for 1 hour and then worked up as described in Example C 18.

Yield: 1.81 g (78%), melting point 187°-192° C. (methanol)

$C_9H_{16}N_2O_5$: calculated: C 46.55; H 6.89; N 12.07; found: C 46.40; H 7.01; N 11.73

24. N-Benzyl-N'-(L-1-carbomethoxy-ethyl)-urea 503 mg of benzylamine are added to 2.15 g of 3-[N-L(1-carbomethoxy-ethyl)-carbamyloxy]-4-hydroxy-2,5-diphenythiophene-1,1-dioxide in 25 ml of ethyl acetate. The solution is boiled under reflux for 1 hour and then worked up as described in Example C 18.

Yield: 979 mg (83%), melting point 175° C. (ethanol)

$C_{12}H_{16}N_2O_3$: calculated: C 61.02; H 6.78; found: C 60.89; H 6.85

25. 1-Diphenyl-carbamylpiperidine 425 mg of piperidine are added to 2.37 g of 3-(N,N-diphenylcarbamyloxy)-4-hydroxy-2,5-diphenylthiophene-1,1-dioxide in 25 ml of acetone. The deep red solution is boiled under reflux for 1 hour and then worked up as described in Example C 18.

Yield: 1.04 g (74.3%), melting point 125° C.

26. Cholesteryl N-benzyl-carbamate 540 mg of benzylamine are added to 3.56 g of O-cholesteryl-O'-(4-hydroxy-2,5-diphenylthiophene-1,1-dioxide)-carbonate in 25 ml of ethyl acetate. The solution is boiled under reflux for 2 hours and then washed three times with 30 ml of concentrated aqueous $NaHCO_3$ solution and three times with 30 ml of 20% strength citric acid solution. The wash liquors are extracted with ethyl acetate and the combined organic phases are dried over magnesium sulfate and evaporated.

Yield: 2.10 g (81%), melting point 153° C. (ethanol)
$C_{35}H_{53}NO_2$: calculated: C 80.92, H 10.21, N 2.70; found: C 80.80, H 10.40, N 2.82

27. Isobutyl N-benzyl-carbamate 370 mg of isobutyl alcohol are added to 2.00 g of O-isobutyl-O'-(4-hydroxy-2,5-diphenylthiophene-1,1-dioxide)-carbonate in 25 ml of ethyl acetate. The solution is boiled under reflux for 2 hours and then worked up as described in Example C 26.

Yield: 859 mg (83%), melting point 88° C. (ethanol)
$C_{12}H_{17}NO_2$: calculated: C 68.39, H 7.77; found: C 68.19, H 7.90

28. Ethyl N-benzyl-carbamate 540 mg of benzylamine are added to 1.86 g of O-ethyl-O'-(4-hydroxy-2,5-diphenylthiophene-1,1-dioxide)-carbonate in 25 ml of ethyl acetate. The mixture is boiled under reflux for 2 hours and then worked up as described in Example C 26.

Yield: 814 mg (91%), melting point 47° C. (ethanol)
$C_{10}H_{13}NO_2$: calculated: C 67.04, H 7.26; found: C 66.98, H 7.31

29. Ethyl N-phenyl-carbamate 465 mg of aniline are added to 1.86 g of O-ethyl-O'-(4-hydroxy-2,5-diphenylthiophene-1,1-dioxide)-carbonate in 25 ml of ethyl acetate. The mixture is boiled under reflux for 2 hours and then worked up as described in Example C 26.

Yield: 734 mg (89%), melting point 52° C. (ethanol)
$C_9H_{11}NO_2$: calculated: C 65.45, H 6.66; found: C 65.39, H 6.65

30. Isopropyl N-phenyl-carbamate 465 mg of aniline are added to 1.93 g of O-isopropyl-O'-(4-hydroxy-2,5-diphenylthiophene-1,1-dioxide)-carbonate in 25 ml of ethyl acetate. The solution is boiled under reflux for 2 hours and then worked up as described in Example C 26.

Yield: 771 mg (86%), melting point 89° C. (ethanol)
$C_{10}H_{13}NO_2$: calculated: C 66.96, H 7.25; found: C 66.78, H 7.32

31. S-Benzyl-thiocarbamylpiperidine 425 mg of piperidine in 10 ml of ethyl acetate are added slowly dropwise to a solution of 2.25 g of O-(3-hydroxy-2,5-diphenylthiophene-1,1-dioxide)-S-benzyl-thiol-carbonate in 20 ml of ethyl acetate. The mixture is boiled under reflux for a further 2 hours and then worked up as described in Example C 26. When the organic phase is evaporated a yellowish colored oil is obtained as the residue and this crystallizes very slowly.

Yield: 930 mg (79%)

32. Methyl isocyanate 1.01 g of triethylamine and 675 mg of methylammonium chloride are added to 3.59 g of 3,4-carbonyldioxy-2,5-diphenylthiophene-1,1-dioxide in 50 ml of o-dichlorobenzene. The solution is heated at 130° C. and the methyl isocyanate formed is immediately distilled off from the reaction mixture.

Yield: 540 mg (95%), boiling point 45° C.

The methyl isocyanate was identified in the form of N-methyl-N'-phenylurea.

$C_8H_{10}N_2O$: calculated: C 64.00, H 6.66; found: C 63.89, H 6.58

33. Phenyl isocyanate 2.1 g of 3-(phenylcarbamyloxy)-4-hydroxy-2,5-diphenylthiophene-1,1-dioxide in 50 ml of o-dichlorobenzene are heated at 150° C. for 2 hours. The phenyl isocyanate formed is then distilled off under reduced pressure produced by a water pump.

Yield: 571 mg (96%), boiling point 60° C./15 mm Hg
$C_7H_5NO$: calculated: C 70.59, H 4.20; found: C 70.40, H 4.35

34. Benzyl isocyanate 2.16 g of 3-(benzylcarbamyloxy)-4-hydroxy-2,5-diphenylthiophene-1,1-dioxide in 50 ml of o-dichlorobenzene are heated at 150° C. for 2 hours. The benzyl isocyanate formed is then distilled off under reduced pressure produced by a water pump.

Yield: 625 mg (94%), boiling point$_{12}$ 88° C.
$C_8H_7NO$: calculated: C 72.18, H 5.26; found: C 71.85, H 5.20

35. L-Carbonyl-alanine methyl ester 2.15 g of 3[N-L-(1-carbomethoxy)-ethyl-carbamyloxy]-4-hydroxy-2,5-diphenylthiophene-1,1-dioxide are heated carefully up to the melting point, under greatly reduced pressure. The isocyanate formed is distilled off direct. The isocyanate formed is distilled off direct.

Yield: 587 mg (91%), boiling point 35° C./0.8 mm Hg
$C_5H_7NO_3$: calculated: C 46.51, H 5.43; found: C 46.39, H 5.50

36. L-Carbonyl-valine methyl ester 2.28 g of 3-[N-L-(1-carbomethoxy-2-methyl)-propyl-carbamyloxy]-4-hydroxy-2,5-diphenylthiophene-1,1-dioxide are heated carefully up to the melting point, under greatly reduced pressure. The isocyanate formed is distilled off direct.

Yield: 699 mg (89%), boiling point 41° C./0.8 mm Hg
$C_7H_{11}NO_3$: calculated: C 53.50, H 7.00; found: C 53.35, H 7.10

37. L-Carbonyl-leucine ethyl ester 2.42 g of 3-[N-L-(1-carbethoxy-3-methyl)-butyl-carbamyloxy]-4-hydroxy-2,5-diphenylthiophene-1,1-dioxide are heated carefully up to the melting point, under greatly reduced pressure. The isocyanate formed is distilled off direct.

Yield: 805 mg (87%), boiling point 51° C./0.8 mm Hg
$[\alpha]_D^{20} = -22.3°$ $C_9H_{15}NO_3$: calculated: C 58.38, H 8.11; found: C 58.25, H 8.10

38. p-Phenylene diisocyanate 504 mg of p-phenylenediamine are added to 3.59 g of 3,4-carbonyldioxy-2,5-diphenylthiophene-1,1-dioxide in 30 ml of o-dichlorobenzene. The solution is boiled under reflux for 2 hours and the solvent is then distilled off. The solid residue is distilled via a heated distillation bridge, under reduce pressure produced by a water pump.

Yield: 520 mg (65%), melting point 93° C., boiling point 108° C./10mmHg literature: melting point 94° C., boiling point 110° C./12 mm Hg.

D. Examples of the preparation of peptides, which can be used as structural units for the synthesis of antamanides:

1. N-tert.-Butoxycarbonyl-L-alanine-L-phenylalanine methyl ester 526 mg of triethylamine are added to a mixture of 942 mg of Boc-Ala$\approx$SO$_2$ (the abbreviation $\approx$SO$_2$ used here and below in the context of the activated aminoacids denotes the radical -3-oxy-4-hydroxy-2,5-diphenylthiophene-1,1-dioxide) and 432 mg of Phe-OMe.HCl in 20 ml of absolute tetrahydrofuran, whereupon the mixture becomes deep red. It is stirred for 1 hour at 20° C. and in the course of 15 minutes the color changes to pale yellow. The solvent is then distilled off and the residue is dissolved in methylene chloride. The solution is washed three times with 20% strength citric acid solution, three times with saturated sodium bicarbonate solution and twice with water, dried over magnesium sulfate and evaporated under reduced pressure.

Yield: 686 mg (98%), melting point 81° C.
calculated: C 61.70, H 7.43, N 8.00; found: C 61.73, H 7.26, N 8.10
$[\alpha]_D^{20} = +6.9° \pm 0.3°$ c = 1, glacial acetic acid

2. L-Alanine-phenylalanine methyl ester hydrochloride (elimination of the Boc group from D 1)

686 mg of the Boc-dipeptide ester D 1 are dissolved in 15.7 ml of 1 N HCl in glacial acetic acid. Thereafter, the solution is stirred for 2 hours at room temperature and then evaporated under reduced pressure. The residue is digested with ether.

Yield: 534 mg (95%), melting point 150° C.
calculated: C 54.45, H 6.64; found: C 54.13, H 6.59
$[\alpha]_D^{20} = -57.3° + 0.5°$ c = 1, glacial acetic acid

3. N-tert.-Butoxycarbonyl-L-proline-alanine-L-phenylalanine methyl ester 447 mg of triethylamine are added to a mixture of 488 mg of Ala-Phe-OMe. HCl D 2 and 845 mg of Boc-Pro$\approx$SO$_2$ in 20 ml of absolute tetrahydrofuran, whereupon the color of the mixture becomes deep red. The mixture is stirred for 1 hour at 20° C. The pale yellow mixture is then worked up as described in Example D 1 and the product is digested with petroleum ether.

Yield: 731 mg (96%), melting point 120° C.
calculated: C 61.50, H 7.37; found: C 61.27, H 7.33

4. L-Proline-L-alanine-L-phenylalanine methyl ester hydrochloride (elimination of the Boc group from D 3)

716 mg of the Boc-tripeptide ester D 3 are dissolved in 12.8 ml of 1 N HCl in glacial acetic acid. Thereafter, the solution is stirred for 2 hours at room temperature and then evaporated under reduced pressure. The resulting oil precipitates as a solid from tetrahydrofuran with petroleum ether.

Yield: 571 mg (93%), amorphous powder
calculated: C 53.80, H 6.98, N 10.45; found: C 54.23, H 6.85, N 10.41
$[\alpha]_D^{20} = -21.0° \pm 0.5°$ c = 1, glacial acetic acid

5. N-tert.-Butoxycarbonyl-L-proline-L-proline-L-alanine-L-phenylalanine methyl ester 341 mg of triethylamine are added to a mixture of 500 mg of Pro-Ala-Phe-OMe.HCl D 4 and 647 mg of Boc-Pro$\approx$SO$_2$ in 20 ml of absolute tetrahydrofuran whereupon the mixture develops a deep red coloration. It is stirred for 1 hour at 20° C. The pale yellow mixture is then worked up as described in Example D 1.

Yield: 657 mg (93%), oil.

6. L-Proline-L-proline-L-alanine-L-phenylalanine methyl ester hydrochloride (elimination of the Boc group from D 5)

600 mg of the Boc-tetrapeptide ester D 5 are dissolved in 8.8 ml of 1 N HCl in glacial acetic acid. Thereafter, the solution is stirred for 2 hours at room temperature and then evaporated under reduced pressure.

Yield: 454 mg (86%), melting point 75° C.
calculated: C 57.43, H 6.92, N 11.65; found: C 57.17, H 6.93, N 11.41

7. N-tert.-Butoxycarbonyl-L-valine-L-proline-L-proline-L-alanine-L-phenylalanine methyl ester 184 mg of triethylamine are added to a mixture of 337 mg of Pro-$_2$-Ala-Phe-OMe.HCl D 6 and 350 mg of Boc-Val$\approx$SO$_2$ in 20 ml of absolute tetrahydrofuran, whereupon the mixture develops a deep red coloration. It is stirred for 2 hours at room temperature. The pale yellow mixture is then worked up as described in Example D 1.

Yield: 400 mg (89%), oil

8. L-Valine-L-proline-L-proline-L-alanine-L-phenylalanine methyl ester hydrochloride (elimination of the Boc group from D 7)

322 mg of the Boc-pentapeptide ester D 7 are dissolved in 4 ml of 1 N HCl in glacial acetic acid. The solution is then stirred for 2 hours at room temperature and evaporated under reduced pressure.

Yield: 202 mg (70%), melting point 127°–129° C.

9. N-tert.-Butoxycarbonyl-L-phenylalanine-L-phenylalanine methyl ester 788 mg of triethylamine are added to a mixture of 648 mg of Phe-OMe.HCl and 1.641 g of Boc-Phe$\approx$SO$_2$ in 20 ml of absolute tetrahydrofuran, whereupon the mixture becomes deep red. It is stirred for 1 hour at 20° C. The pale yellow mixture is then worked up as described in Example D 1.

Yield: 1,250 mg (98%), melting point 132° C.

10. L-Phenylalanine-L-phenylalanine methyl ester hydrochloride (elimination of the Boc group from D 9)

1,200 mg of the Boc-dipeptide ester D 9 are dissolved in 22.5 ml of 1 N HCl in glacial acetic acid. The mixture is then stirred for 2 hours at room temperature and evaporated under reduced pressure.

Yield: 988 mg (97%), melting point 193° C.

calculated: C 62.85, H 6.39, N 7.72; found: C 62.85, H 6.70, N 7.70

11.

N-tert.-Butoxycarbonyl-L-proline-L-phenylalanine-L-phenylalanine methyl ester 687 mg of triethylamine are added to a mixture of 944 mg of Phe-Phe-OMe.HCl D 10 and 1,293 mg of Boc-Pro≈SO₂ in 20 ml of absolute tetrahydrofuran, whereupon the mixture develops a deep red coloration. It is stirred for 1 hour at 20° C. The pale yellow mixture is then worked up as described in Example D 1.

Yield: 1,317 mg (97%), melting point 115° C.

calculated: C 66.50, H 7.08, N 8.03; found: C 66.55, H 7.23, N 7.95

12. L-Proline-L-phenylalanine-L-phenylalanine methyl ester hydrochloride (elimination of the Boc group from D 11)

1,255 mg of the Boc-tripeptide ester D 11 are dissolved in 19 ml of 1 N HCl in glacial acetic acid. Thereafter, the mixture is stirred for 2 hours at room temperature and then evaporated under reduced pressure.

Yield: 1,011 mg (92%), amorphous powder

13.

N-tert.-Butoxycarbonyl-L-proline-L-proline-L-phenylalanine-L-phenylalanine methyl ester 552 mg of triethylamine are added to a mixture of 965 mg of Pro-Phe-Phe-OMe.HCl D 12 and 1,044 mg of Boc-Pro≈SO₂ in 20 ml of absolute tetrahydrofuran, whereupon the mixture develops a deep red coloration. It is stirred for 1.5 hours at 20° C. The pale yellow mixture is then worked up as described in Example D 1.

Yield: 1,183 mg (91%), oil calculated: C 65.78, H 7.14; found: C 65.61, H 6.83

14.

L-Proline-L-proline-L-phenylalanine-L-phenylalanine methyl ester hydrochloride (elimination of the Boc group from D 13)

1,116 mg of the Boc-tetrapeptide ester D 13 are dissolved in 14.4 ml of 1 N HCl in glacial acetic acid. The mixture is then stirred for 2 hours at room temperature and evaporated under reduced pressure.

Yield: 910 mg (91%), amorphous powder

15.

N-tert.-Butoxycarbonyl-L-phenylalanine-L-proline-L-proline-L-phenylalanine-L-phenylalanine methyl ester 420 mg of triethylamine are added to a mixture of 891 mg of Pro-Pro-Phe-Phe-OMe.HCl D 14 and 875 mg of Boc-Phe≈SO₂ in 20 ml of absolute tetrahydrofuran, whereupon the mixture develops a deep red coloration. It is stirred for 2 hours at 20° C. The pale yellow mixture is then worked up as described in Example D 1.

Yield: 1,080 mg (88%), melting point 78°–80° C.

calculated: C 67.30, H 67.08; found: 6.90, H 6.96

We claim:

1. Cyclic esters of 3,4-dihydroxy-2,5-diphenylthiophene-1,1-dioxide of the formula (1)

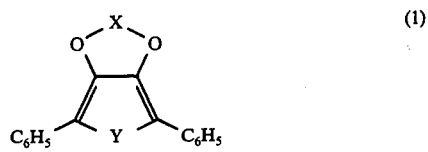

where X is $>C=O$, $>C=S$, or

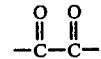

and Y is $>SO_2$.

2. 3,4-Carbonyl-dioxy-2,5-diphenyl-thiophene-1,1-dioxide.

3. A cyclic ester as claimed in claim 1 wherein X is $>C=S$.

4. A cyclic ester as claimed in claim 1 wherein X is

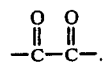

* * * * *